United States Patent [19]
Wickham et al.

[11] Patent Number: 5,559,099
[45] Date of Patent: Sep. 24, 1996

[54] PENTON BASE PROTEIN AND METHODS OF USING SAME

[75] Inventors: Thomas J. Wickham, Gaithersburg; Imre Kovesdi, Rockville; Douglas E. Brough, Olney; Duncan L. McVey, Derwood; Joseph T. Brader, New Market, all of Md.

[73] Assignee: GenVec, Inc., Rockville, Md.

[21] Appl. No.: 303,162

[22] Filed: Sep. 8, 1994

[51] Int. Cl.$^6$ .......................... C12P 21/04; C12N 15/00; C12N 7/00
[52] U.S. Cl. .................. 514/44; 435/69.7; 435/172.1; 435/235.1; 435/320.1; 935/57
[58] Field of Search ........................ 514/44; 935/57; 435/69.1, 69.7, 172.1, 235.1, 320.1

[56] References Cited

FOREIGN PATENT DOCUMENTS

WO92/13081  8/1992  WIPO .......................... C12N 15/70
WO94/17832  8/1994  WIPO .......................... A61K 48/00

OTHER PUBLICATIONS

Albiges–Rizo et al., "Human adenovirus serotype 3 fiber protein. Somparison of native and recombinant proteins," *J. Biol. Chem.*, 266 (6), 3961–3967 (1991).

Hong et al., "The amino terminus of the adenovirus fiber protein encodes the nuclear localization signal," *Virology*, 185 (2), 758–767 (1991).

Novelli et al., "Deletion analysis of functional domains in Baculovirus–expressed Adenovirus type 2 fiber," *Virology*, 185 (1), 365–376 (1991).

Wickham et al., "Targeting of adenovirus penton base to new receptors through replacement of its RGD motif with other receptor–specific peptide motifs," *Gene Ther.*, 2 (10), 750–756 (1995).

Ball–Goodrich et al., Parvoviral Target Cell Specificity: Acquisition of fibrotropism by a mutant of the lymphotropic strain of minute virus involves multiple amino acid substitutions within the capsid, Virology 184: 175–186.

Horvath et al., "Nonpermissivity of Human Peripheral Blood Lymphocytes to Adenovirus Type 2 Infection," *Journal of Virology*, 62 (1), 341–345 (1988).

Komoriya et al., "The Minimal Essential Sequence for a Major Cell Type–Specific Adhesion Site (CS1) Within the Alternately Spliced Type III Connecting Segment Domain of Fibronectin Is Leucine–Aspartic Acid–Valine," *The Journal of Biological Chemistry*, 266 (23), 15075–15079 (1991).

Mathias et al., "Multiple Adenovirus Serotypes Use $\alpha v$ Integrins For Infection," *Journal of Virology*, 68 (10), 6811–6814 (1994).

Nemerow et al., "Adenovirus Entry Into Host Cells: A Role For $\alpha_v$ Integrins," *Trends In Cell Biology*, 4, 52–55 (1994).

Nemerow et al., "The Role of $\alpha v$ Integrins In Adenovirus Infection," *Biology of Vitronectins and Their Receptors*, Elsevier Science Pub., Preissner et al., eds., 177–184.

Silver et al., "Interaction of Human Adenovirus Serotype 2 With Human Lymphoid Cells," *Virology*, 165, 377–387 (1988).

Stewart et al., "Difference Imaging of Adenovirus: Bridging The Resolution Gap Between X–Ray Crystallography And Electron Microscopy," *The EMBO Journal*, 12 (7), 2589–2599 (1993).

Wickham et al., "Integrins $\alpha_v\beta_3$ and $\alpha_v\beta_5$ Promote Adenovirus Internalization But Not Virus Attachment," *Cell*, 73, 309–319 (1993).

Bai et al., "Mutations That Alter an Arg–Gly–Asp (RGD) Sequence in the adenovirus Type 2 Penton Base Protein Abolish Its Cell–Rounding Activity and Delay Virus Reproduction in Flat Cells," *Journal of Virology*, 67 (9), 5198–5205 (1993).

Cotten et al., "High–Efficiency Receptor–Mediated Delivery of Small and Large (48 Kilobase) Gene Constructs Using the Endosome–Disruption Activity of Defective or Chemically Inactivated Adenovirus Particles," *Proc. Natl. Acad. Sci. USA*, 89, 6094–6098 (1992).

Curiel et al., "High–Efficiency Gene Transfer Mediated By Adenovirus Coupled to DNA–Polylysine Complexes," *Human Gene Therapy*, 3, 147–154 (1992).

Greber et al., "Stepwise Dismantling of Adenovirus 2 During Entry Into Cells," *Cell*, 75, 477–486 (1993).

*Primary Examiner*—Mindy B. Fleisher
*Assistant Examiner*—Bonnie D. Weiss
*Attorney, Agent, or Firm*—Leydig, Voit & Mayer, Ltd.

[57] ABSTRACT

A recombinant adenovirus comprising a chimeric penton base protein, which includes a nonpenton base sequence, and a therapeutic gene, a method of gene therapy involving the use of such adenovirus, and adenoviral transfer vectors for the generation of such recombinant adenovirus are provided.

35 Claims, 2 Drawing Sheets

SpeI    New Sequence
GACATGAACGATACTAGTGCCACACGGGCT [SEQ ID NO:9]
▲AspMetAsnAspThrSerAlaThrArgAla [SEQ ID NO:10]

Wild-type Sequence
4584 GACATGAACGATCATGCCATTCGCGGGGACACCTTTGCCACACGGGCT [SEQ ID NO:1]
   1▶AspMetAsnAspHisAlaIleArgGlyAspThrPheAlaThrArgAla [SEQ ID NO:12]
                        1▶ArgGlyAsp [SEQ ID NO:11]

PENTON BASE PROTEIN AND METHODS OF USING SAME

TECHNICAL FIELD OF THE INVENTION

The present invention relates to a recombinant adenovirus comprising a chimeric adenoviral penton base protein and the use of a recombinant adenovirus comprising a chimeric adenoviral penton base protein in gene therapy.

BACKGROUND OF THE INVENTION

Adenoviruses belong to the family Adenoviridae, which is divided into two genera, namely Mastadenovirus and Aviadenovirus. Adenoviruses are nonenveloped, regular icosahedrons 65–80 nm in diameter (Horne et al., *J. Mol. Biol.*, 1, 84–86 (1959)). The capsid is composed of 252 capsomeres of which 240 are hexons and 12 are pentons (Ginsberg et al., *Virology*, 28, 782–783 (1966)). The hexons and pentons are derived from three different viral polypeptides (Maizel et al., *Virology*, 36, 115–125 (1968); Weber et al., *Virology*, 76, 709–724 (1977)). The hexon comprises three identical polypeptides of 967 amino acids each, namely polypeptide II (Roberts et al., *Science*, 232, 1148–1151 (1986)). The penton contains a penton base, which is bound to the capsid, and a fiber, which is noncovalently bound to and projects from the penton base. The fiber protein comprises three identical polypeptides of 582 amino acids each, namely polypeptide IV. The Ad2 penton base protein is an 8×9 nm ring-shaped complex composed of five identical protein subunits of 571 amino acids each, namely polypeptide III (Boudin et al., *Virology*, 92, 125–138 (1979)). Proteins IX, VI, and IIIa are also present in the adenovirus coat and are thought to stabilize the viral capsid (Stewart et al., *Cell*, 67, 145–154 (1991); Stewart et al., *EMBO J.*, 12(7), 2589–2599 (1993)).

Once an adenovirus attaches to a cell, it undergoes receptor-mediated internalization into clathrin-coated endocytic vesicles of the cell (Svensson et al., *J. Virol.*, 51, 687–694 (1984); Chardonnet et al., *Virology*, 40, 462–477 (1970)). Virions entering the cell undergo a stepwise disassembly in which many of the viral structural proteins are shed (Greber et al., *Cell*, 75, 477–486 (1993)). During the uncoating process, the viral particles cause disruption of the cell endosome by a pH-dependent mechanism (Fitzgerald et al., *Cell*, 32, 607–617 (1983)), which is still poorly understood. The viral particles are then transported to the nuclear pore complex of the cell (Dales et al., *Virology*, 56, 465–483 (1973)), where the viral genome enters the nucleus, thus initiating infection.

An adenovirus uses two separate cellular receptors, both of which must be present, to attach to and efficiently infect a cell (Wickham et al., *Cell*, 73, 309–319 (1993)). First, the fiber protein attaches the virus to a cell by binding to an, as yet, unidentified receptor. Then, the penton base binds to $\alpha_v$ integrins. Integrins are a family of heterodimeric cell surface receptors that mediate cellular adhesion to the extracellular matrix molecules fibronectin, vitronectin, laminin, and collagen, as well as other molecules (Hynes, *Cell*, 69, 11–25 (1992)). Integrins are known to play important roles in cell signaling processes, including calcium mobilization, protein phosphorylation, and cytoskeletal interactions (Hynes, supra). The specificity with which an integrin binds to a particular ligand, such as those associated with an adenovirus, is a function of the paired $\alpha$ and $\beta$ subunits of the integrin. For example, integrin $\alpha_6\beta_1$ binds to laminin, integrin $\alpha_2\beta_1$ binds to collagen and laminin, and integrin $\alpha_3\beta_1$ binds to collagen, laminin, and fibronectin. Furthermore, different tissue types may have different complements of integrin subunits, thereby providing a mode of spatial control over integrin-ligand signal transfer or over ligand internalization. Accordingly, some integrins, such as those that include subunit $\alpha_v$, are broadly expressed on numerous cell types, whereas other integrins have a much more narrow tissue distribution. For example, the integrins that include subunit $\beta_2$ are expressed only on leukocytes, such as neutrophils and macrophages, integrins including subunit $\alpha_4$ are expressed only on lymphocytes and fibroblasts, and the integrin defined by the subunits $\alpha_{IIb}62_3$ is expressed only on platelets and megakaryocytes.

The specificity of integrin subunit complement also extends to the infectability of cells by different serotypes of adenovirus, because the particular $\alpha$ and $\beta$ subunits dictate whether a virus can enter a cell. For example, the penton base of the adenovirus serotype Ad2 binds to integrins $\alpha_v\beta_3$ and $\alpha_v\beta_5$ (Wickham et al. (1993), supra). Given that both receptors utilized by an adenovirus are expressed on most human cells, nearly all cells in a human body are susceptible to adenoviral infection.

A majority of integrins have been found to recognize short linear stretches of amino acids in binding to a specific ligand. The tripeptide motif arg-gly-asp (RGD) [SEQ ID NO:1], which is found in scores of matrix ligands, including laminin, fibronectin, collagen, vitronectin, and fibrinogen, has been implicated in the binding of $\alpha_3\beta_1$, $\alpha_5\beta_1$, $\alpha_{IIb}\beta_3$, $\alpha_m\beta_2$, and most, if not all, of the five $\alpha_v$-containing integrins. The conformation of the RGD sequence within a matrix ligand is thought to be a primary factor in integrin specificity (Pierschbacher et al., *J. Biol. Chem.*, 262, 17294–17298 (1987)). Sequences that directly flank the RGD sequence have been shown to influence integrin specificity, presumably because of their effect on RGD conformation (Smith et al., *Proc. Natl. Acad. Sci. USA*, 90, 10003–10007 (1993)). However, sequences distant from the RGD may also function in integrin specificity as has been shown for the binding of $\alpha_5\beta_1$ to fibronectin (Obara et al., *Cell*, 53, 649–657 (1988)). Other integrins, which do not utilize RGD, have been found to bind similar short linear stretches of amino acids within their specific ligands. For example, integrin $\alpha_{IIb}\beta_3$ binds via the amino acid sequence lys-gln-ala-gly-asp (KQAGD) [SEQ ID NO:2] in fibrinogen (Kloczewiak et al., *Biochemistry*, 23, 1767–1774 (1984)), while $\alpha_4\beta_1$ binds via the core sequence glu-ile-leu-asp-val (EILDV) [SEQ ID NO:3] in fibronectin (Komoriya et al., *J. Biol. Chem.*, 266, 15075–15079 (1991)). A structural motif (i.e., asn-pro-xaa-tyr (NPXY) [SEQ ID NO:4]) present in the $\beta$ subunits of $\alpha_v$-containing integrins has been shown to be important for internalization (Suzuki et al., *Proc. Natl. Acad. Sci. USA*, 87, 5354 (1990)).

The penton base sequence is highly conserved among serotypes of adenovirus and contains five copies of the RGD tripeptide motif (Neumann et al., *Gene*, 69, 153–157 (1988)). The RGD tripeptide is believed to mediate binding to $\alpha_v$ integrins because exogenously added RGD peptides can block penton base binding and adenoviral infection (Wickham et al. (1993), supra), and adenoviruses that have point mutations in the RGD sequence of the penton base are restricted in their ability to infect cells (Bai et al., *J. Virol.*, 67, 5198–5205 (1993)).

The penton base genes from Ad2, Ad5, Ad12, and Ad40 serotypes of adenovirus have been sequenced. Alignment of the sequences reveals a high degree of conservation over the entire sequence, except for the N-terminus, and, in Ad2, Ad5, and Ad12, a hypervariable region that includes the RGD sequence. Only Ad40, one of two enteric adenoviral serotypes, does not have an RGD sequence. Ad2 and Ad5 are identical in the hypervariable region and contain a large insert of amino acids flanking either side of the RGD sequence. Secondary structural analysis of the hypervariable regions of the three RGD-containing penton bases predicts that, in each case, the RGD is flanked by α-helices. Such structures are believed to form the spikes seen in cryoelectron micrographic (cryo-EM) images of Ad2 penton bases (Stewart et al. (1993), supra).

Recombinant adenoviral vectors have been used for the cell-targeted transfer of one or more recombinant genes to diseased cells or tissue in need of treatment. Such vectors are characterized by the further advantage of not requiring host cell proliferation for expression of adenoviral proteins (Horwitz et al., *In Virology*, Raven Press, New York, vol. 2, pp. 1679–1721 (1990); and Berkner, *BioTechniques*, 6, 616 (1988)), and, if the targeted tissue for somatic gene therapy is the lung, these vectors have the added advantage of being normally trophic for the respiratory epithelium (Straus, *In Adenoviruses*, Plenan Press, New York, pp. 451–496 (1984)).

Other advantages of adenoviruses as potential vectors for human gene therapy are as follows: (i) recombination is rare; (ii) there are no known associations of human malignancies with adenoviral infections despite common human infection with adenoviruses; (iii) the adenoviral genome (which is a linear, double-stranded DNA) can be manipulated to accommodate foreign genes that range in size; (iv) an adenoviral vector does not insert its DNA into the chromosome of a cell, so its effect is impermanent and unlikely to interfere with the cell's normal function; (v) the adenovirus can infect nondividing or terminally differentiated cells, such as cells in the brain and lungs; and (vi) live adenovirus, having as an essential characteristic the ability to replicate, has been safely used as a human vaccine (Horwitz et al. (1990), supra; Berkner et al. (1988), supra; Straus et al. (1984), supra; Chanock et al., *JAMA*, 195, 151 (1966); Haj-Ahmad et al., *J. Virol.*, 57, 267 (1986); and Ballay et al., *EMBO*, 4, 3861 (1985)).

The problem of using a recombinant adenovirus in gene therapy is that all cells that express the aforementioned two receptors used by the adenovirus to attach and infect a cell will internalize the gene(s) being administered—not just the cells in need of therapeutic treatment. Likewise, certain cells, such as lymphocytes, which lack the $\alpha_v$ integrin adenoviral receptors, will be severely impaired in the uptake of an adenovirus and will not be easily amenable to adenovirus-mediated gene delivery. Accordingly, limiting adenoviral entry to specific cells and/or expanding the repertoire of cells amenable to adenovirus-mediated gene therapy would be a significant improvement over the current technology. Targeted adenoviral gene delivery should expand the cells amenable to gene therapy, reduce the amount of adenoviral vector that is necessary to obtain gene expression in the targeted cells, as well as reduce side effects and complications associated with increasing doses of an adenovirus, such as inflammation and the transfection of normal, healthy cells.

Attempts have been made to target a virus to specific cells by sterically blocking adenoviral fiber protein with antibodies and chemically linking tissue-specific antibodies to the viral particle (Cotten et al., *Proc. Natl. Acad. Sci. USA*, 89, 6094–6098 (1992)). Although this approach has demonstrated the potential of targeted gene delivery, the complexity and reproducibility of this approach present major hurdles blocking its application in clinical trials. The difficulties thus far encountered in targeting the virus by these methods involve the method of synthesis required, which is to make major alterations in the viral particles following their purification. These alterations involve additional steps that covalently link large molecules, such as polylysine, receptor ligands and antibodies, to the virus. The targeted particle complexes are not homogeneous in structure and their efficiency is sensitive to the relative ratios of viral particles, linking molecules, and targeting molecules used.

The present invention seeks to overcome the problem of lack of cell and tissue specificity of recombinant adenoviral gene therapy. It is an object of the present invention to provide a receptor-specific, preferably cell receptor-specific/tissue receptor-specific, recombinant adenovirus. A further object of the present invention is to provide means for generating such a recombinant adenovirus at the level of gene expression, thereby enabling purification of recombinant adenoviral particles by conventional techniques. Another object of the present invention is to provide a method of gene therapy involving the use of such a homogeneous adenovirus, without the need for additional components or further modification. These and other objects and advantages of the present invention, as well as additional inventive features, will be apparent from the following detailed description.

BRIEF SUMMARY OF THE INVENTION

The present invention provides a recombinant adenovirus comprising a chimeric penton base protein that selectively binds to a given receptor, preferably a cell-specific/tissue-specific receptor, an adenoviral transfer vector comprising a recombinant penton base gene for the generation of a chimeric penton base protein, and a method of using a receptor-specific recombinant adenovirus comprising a therapeutic gene in gene therapy.

DETAILED DESCRIPTION OF THE INVENTION

The present invention provides, among other things, a recombinant adenovirus comprising a chimeric penton base protein. The chimeric penton base protein comprises a nonpenton base amino acid sequence, which is specific for binding to a receptor, a receptor-specific antibody domain or epitope, in addition to or in place of a wild-type penton base amino acid sequence, preferably an amino acid sequence that is specific for binding to a receptor, most preferably an RGD amino acid sequence.

By "nonpenton base amino acid sequence" is meant any amino acid sequence that is not found in a wild-type penton base. Preferably, the nonpenton base sequence is less than ten amino acids, more preferably less than five amino acids, and most preferably about three amino acids. By "RGD amino acid sequence" is meant the RGD amino acid sequence and the RGD amino acid sequence along with up to or including three amino acids flanking either or both sides of the RGD amino acid sequence. The nonpenton base amino acid sequence renders the adenovirus specific for a given receptor, preferably a cell-specific or tissue-specific receptor, or specific for a given receptor-specific antibody domain or epitope. The receptor is preferably one that the wild-type adenovirus does not bind or one that the wild-type adenovirus binds but with greater specificity upon the introduction of the nonpenton base amino acid sequence into the chimeric penton base protein.

Preferably, the RGD amino acid sequence of the penton base protein has been replaced at the DNA level with an amino acid binding sequence for a given receptor, receptor-specific antibody domain or epitope. Alternatively, the RGD amino acid sequence has been rendered inactive at the DNA level by mutation of the RGD amino acid sequence, such as by insertional mutagenesis, for example, or rendered conformationally inaccessible in the penton base protein, such as by insertion of a DNA sequence into or adjacent to the adenoviral penton base gene sequence, wherein "gene sequence" refers to the complete penton base gene sequence as well as any lesser gene sequences that are capable of being expressed as functional penton base protein. Preferably, the DNA sequence is inserted near the gene sequence encoding the RGD amino acid sequence, so as to move the gene sequence encoding the RGD amino acid sequence within the penton base gene sequence such that in the chimeric penton base protein the RGD amino acid sequence is conformationally inaccessible for binding to a receptor. In the latter case, the inserted nonpenton base gene sequence that causes the conformational inaccessibility of the RGD amino acid sequence in the penton base protein is preferably one that encodes an amino acid sequence that is specific for binding to a receptor, a receptor-specific antibody domain or epitope. Such a recombinant adenovirus can be used, for example, to study receptor binding, adenoviral attachment, and adenoviral infection in vitro or in vivo.

In a preferred embodiment of the present invention, the above-described recombinant adenovirus additionally comprises a gene capable of being expressed in a cell to which the virus has attached or by which the virus has been internalized and preferably is one having therapeutic utility. In yet another preferred embodiment of the present invention, the recombinant adenovirus is fiberless or further comprises a chimeric coat protein, such as a fiber or hexon, that includes an amino acid sequence that is specific for a receptor, a receptor-specific antibody domain or epitope, preferably one that is specific for the same receptor, antibody domain or epitope as the nonpenton base sequence. Such recombinant adenovirus can be used, for example, to study the effects of expression of the gene in a given cell or tissue in vitro or in vivo. Alternatively, the recombinant adenovirus can be used for gene therapy.

The recombinant adenovirus comprising a chimeric penton base protein and the recombinant adenovirus that additionally comprises a gene capable of being expressed in a particular cell can be generated by use of a viral transfer vector, preferably an adenoviral transfer (pAT) vector, in accordance with the present invention. The viral transfer vector, preferably the pAT vector, comprises a chimeric adenoviral penton base gene sequence. The chimeric penton base gene sequence comprises a nonpenton base sequence in place of the RGD amino acid sequence, which has been deleted, or in addition to the RGD amino acid sequence, which has been mutated or rendered conformationally inaccessible in the expressed chimeric penton base protein as described above. The nonpenton base sequence renders the adenovirus specific for binding to a receptor, receptor-specific antibody domain or epitope also as described above. Given that the penton base gene has been shown to be >90% conserved among 5 of the approximately 41 serotypes of adenovirus, it is expected that any one of the serotypes of adenovirus may be used as the source of the penton base gene. It is preferred, however, that one of the serotypes for which the penton base gene has been sequenced is used.

Restriction sites that are unique with respect to the adenoviral genome are introduced into the penton base gene sequence; preferably, such restriction sites are introduced into or flanking the RGD region of the penton base gene sequence by a suitable method, such as PCR mutagenesis. These unique restriction sites may be any restriction site not already present in the penton base gene, and are preferably Eco RI and/or Spe I. Such sites facilitate the removal, inactivation, such as by sequence alteration, of the DNA sequence encoding the RGD amino acid sequence in a given adenoviral genome, such as a wild-type adenovirus, or the rendering of the RGD amino acid sequence conformationally inaccessible, thereby altering or eliminating the ability of the penton base molecule to bind an $\alpha_v$ integrin receptor. A deleted RGD amino acid sequence can be replaced with, or a mutated or conformationally inaccessible RGD sequence can be accompanied by, a different DNA sequence, preferably a DNA sequence encoding specificity for binding to a receptor, preferably a cell-specific or tissue-specific cell-surface receptor, or to a receptor-specific antibody domain or epitope, for example.

Figure 1:
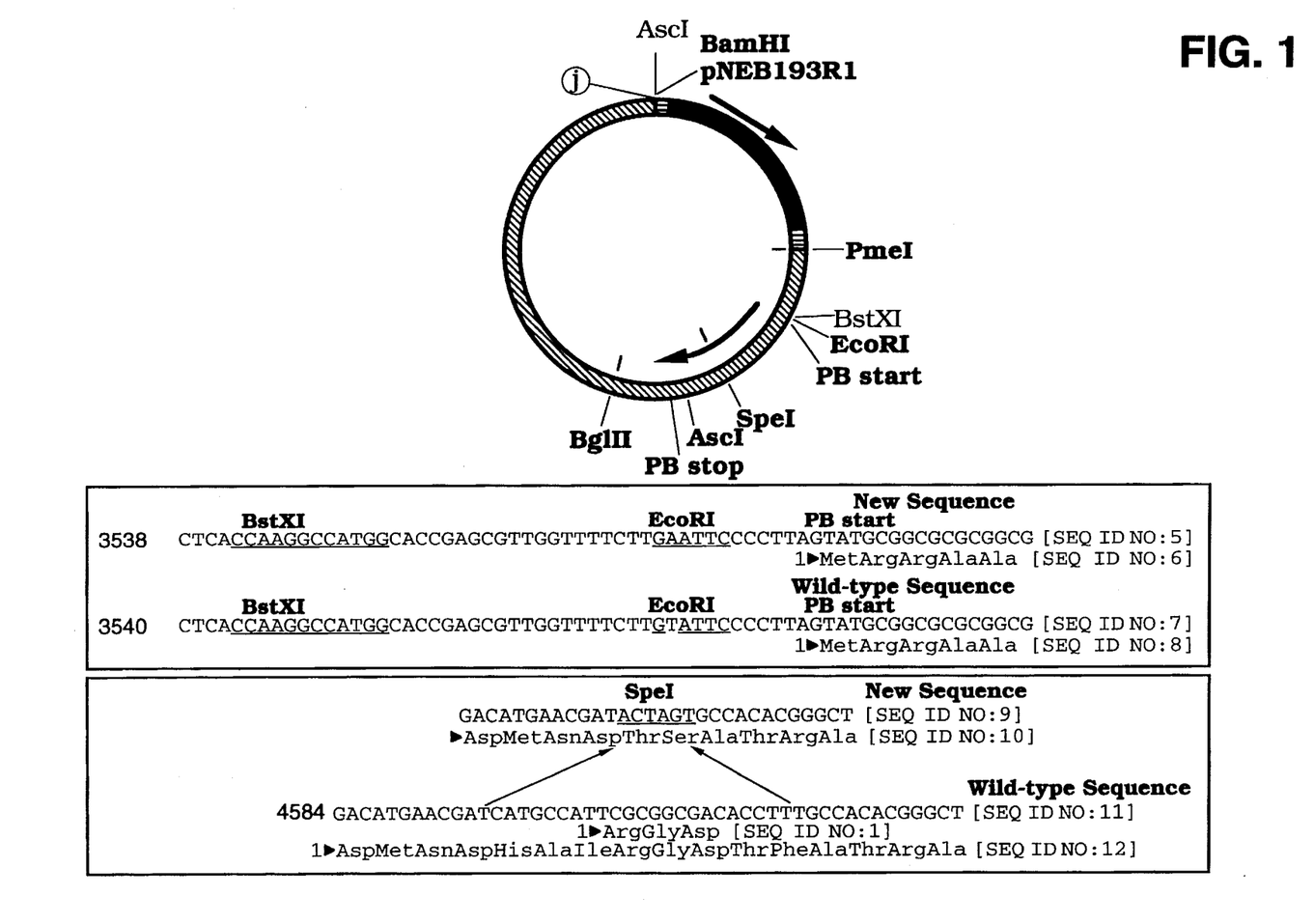
FIG. 1 is a partial restriction map of an adenoviral transfer vector (pAT).

Preferably, the pAT vector is one into which any suitable receptor-specific sequence can be rapidly inserted. For example, a unique Spe I restriction site can be used to remove the RGD amino acid sequence. Alternatively, sequences also can be inserted into the penton base gene sequence without the need for unique restriction sites through PCR. Because a recombinant adenovirus can be created via ligation of recombinant sequences with viral DNA or via homologous recombination, the pAT vector preferably has either (1) unique restriction sites that allow ligation of a vector fragment with the complementing fragments of the remaining viral genomes, as described in Example 4, or (2) adequate lengths of DNA on either side of the receptor-specific or antibody domain- or epitope-specific sequence that allow efficient homologous recombination with viral DNA, as described in Example 5. A preferred pAT vector is shown in FIG. 1, which is a partial restriction map of such a vector. The pAT of FIG. 1 was generated as described in Example 1.

DNA encoding short peptide sequences or protein domains capable of binding to a given receptor, preferably a specific cell or tissue receptor, and capable of being internalized by the receptor, such as the receptor that is resident on leukocytes, is preferred for insertion into the penton base gene sequence in which the RGD amino acid sequence has been deleted, mutated, or rendered conformationally inaccessible. However, other DNA sequences, such as those that encode receptor-specific antibody domains and sequences that encode antigenic epitopes recognized by specific antibodies also may be used to replace the RGD amino acid sequence.

The size of the DNA used to replace the RGD amino acid sequence may be constrained, for example, by impeded folding of the penton base and improper assembly of the penton base/fiber complex. However, cryo-EM analysis of the penton base indicates that, if the RGD amino acid sequence exists at the spikes of the penton bases, there may be considerable room to accommodate large inserts without folding or assembly being affected adversely. Also, the large differences in size between the hypervariable region of the Ad5 penton base and the Ad12 penton base indicates that the hypervariable region may be able to accommodate inserts of various sizes. Of course, assembly of the penton complex probably will not be an issue with respect to viruses that are constructed without a fiber molecule.

The target receptor can be any receptor that is internalized by a cell, is optimally cell-specific or tissue-specific, and desirably is expressed only on those cells or tissue to be treated. Tissue-specific integrins are preferred target receptors for chimeric penton base molecules for four reasons. First, many integrins bind ligands via short linear stretches of amino acids, and these stretches have been identified for many integrins. Second, certain integrins are tissue-specific for cells amenable to targeted gene therapy. For example, $\alpha_2$-containing integrins are expressed only in leukocytes, thus allowing targeted delivery to normally non-susceptible target cells while also preventing delivery to normally susceptible non-target cells. Third, the wild-type penton base uses $\alpha_v$ integrins to enter cells so that the use of a related integrin molecule is more apt to be successful than the use of an unrelated receptor. Fourth, integrins are efficiently internalized into the cell (Bretscher, *EMBO*, 11, 405–410 (1992)), which is required for viral infection of cells.

Changing the penton base protein such that it recognizes a receptor, such as a cell-specific or tissue-specific cell-surface receptor, typically will not alter viral particle attachment to cells because cell attachment is mediated by the adenoviral fiber protein. Infection of the cells to which the chimeric penton base protein has attached, however, will be generally impeded because the virus requires the presence of an $\alpha_v$ integrin to enter the cell. Therefore, an adenovirus with altered penton bases will bind to most cells but will enter only those cells expressing the receptor (e.g., the integrin) for the chimeric penton base. Those cells unable to express the appropriate receptor nonetheless will have adenoviral particles tethered on the cell membrane because the viral particles will be unable to enter the cell. Consequently, tethered adenoviral particles will be exposed to the immune system and disposed of accordingly.

Following fiber-mediated viral attachment to cells, it is possible that some virus may manage to non-specifically enter cells not expressing the cell- or tissue-specific receptor recognized by the chimeric penton base. Therefore, some leakiness in cell-specific or tissue-specific expression may be observed. However, if this is the case, fiber-deficient viral particles can be constructed that use the penton base as the primary cell attachment protein. It is known that fiber protein is nonessential for virion assembly or infectivity of cells (Falgout et al., *J. Virology*, 62, 622–625 (1988)). Such mutant adenoviral particles lacking fiber protein adsorb onto cells at a ten-fold lower rate. The fact that the mutant viruses do adsorb and at a lower rate than wild-type particles indicates that the adsorption is mediated by the penton base/$\alpha_v$ integrin interaction, which has a 30-fold lower affinity than the fiber/fiber-receptor interaction (Wickham et al. (1993), supra). Accordingly, both attachment and internalization can be restricted only to those cells expressing the desired tissue-specific receptor.

By replacing the low affinity RGD amino acid sequence in a wild-type penton base with an amino acid sequence with a high affinity for a given receptor, such as a cell-specific or tissue-specific receptor, it is possible to generate a fiberless viral particle with as high, or higher, affinity for targeted cells than the wild-type fiber-expressing virus. Fiberless viral particles containing a chimeric penton base, compared to fiber-containing viral particles, can be targeted more effectively to tissues because the altered virus is able to bind only to the cells expressing the cell-specific or tissue-specific receptor recognized by the chimeric penton base. The desired ligand and receptor characteristics are as described above.

A recombinant chimeric penton base gene sequence can be moved from a pAT vector into baculovirus or a suitable prokaryotic or eukaryotic expression vector for expression and evaluation of receptor specificity, avidity, and other biochemical characteristics. Accordingly, the present invention also provides recombinant baculoviral and prokaryotic and eukaryotic expression vectors comprising a chimeric adenoviral penton base gene sequence. The chimeric penton base gene sequence includes a nonpenton base sequence in addition to or in place of a wild-type penton base amino acid sequence, such as an RGD amino acid sequence, which is specific for binding to a receptor. The wild-type penton base amino acid sequence may be deleted, mutated, or rendered conformationally inaccessible as described above with respect to the recombinant adenovirus comprising a chimeric penton base protein. By moving the chimeric gene from pAT to baculovirus or a prokaryotic or eukaryotic expression vector, high protein expression is achievable, resulting in approximately 50% of the total protein of the host being the chimeric penton base. Accordingly, the present invention also provides a recombinant baculovirus comprising a chimeric penton base protein and a chimeric adenoviral penton base protein comprising a nonpenton base amino acid sequence in addition to or in place of a wild-type penton base amino acid sequence, such as an RGD amino acid sequence, which is specific for binding to a receptor. The nonpenton base amino acid sequence is specific for binding to a receptor or a receptor-specific antibody domain or epitope as described above. For protein characterization studies, the recombinant chimeric penton base protein (rcPB protein, such as rcPB5) can be purified using any suitable methods, such as those described by Wickham et al. (1993), supra.

Various characteristic parameters of the penton base protein of interest can be assessed as follows: Adhesion assays are used to evaluate the specificity of the interaction of the rcPB protein with its designated receptor, using the method of Wickham et al. (1993), supra, for example. Specificity and affinity of the receptor/rcPB interaction is assessed by Scatchard analysis as shown previously by Wickham et al. (1993), supra, for wild-type penton base protein. Receptor specificity is further assessed by using antibodies and peptides specific for the targeted receptor to block rcPB5 binding to cells, using conventional methods. Internalization is assayed with rcPB protein and recombinant adenoviruses, e.g., Ad5 rcPB, as described previously by Wickham et al. (1993), supra, for example. rcPB binding to fiber protein is assessed by its ability to precipitate radiolabeled fiber molecules when coupled to protein A-coated beads via an antibody to the penton base molecule. Alternatively, fiber binding can be assessed in an ELISA-based assay in which rcPB is coated onto ELISA plates followed by incubation of immobilized rcPB with soluble fiber molecules, using conventional methods. Fiber binding to the rcPB protein is then assessed by a further incubation with antibody specific for the fiber molecule, via conventional techniques.

Virus entry and gene expression are evaluated initially by using the pAT vector containing the insert of interest to generate recombinant virus expressing the chimeric penton base protein and a marker gene, such as β-glucuronidase. β-glucuronidase expression in cells infected with adenovirus containing the β-glucuronidase gene (Ad-Gluc) can be detected as early as two hours after adding Ad-Gluc to cells. This procedure provides a quick and efficient analysis of cell entry of the recombinant virus and gene expression, and is implemented readily by an artisan of ordinary skill using conventional techniques.

A recombinant virus, which lacks a wild-type receptor binding sequence, such as the RGD amino acid sequence, in the penton base protein, can be produced in human embryonic cell line 293 (HEK 293), which has been shown to be able to replicate recombinant adenoviral particles lacking the RGD sequence, using previously described techniques (Bai et al. (1993), supra). A recombinant virus, which lacks functional fiber proteins and in which the penton base acts as both the viral attachment and internalization protein, may be produced in cell lines which express the receptor to which the rcPB5 protein is targeted. For example, Ad5 rcPB5 containing an insert specific for $\alpha_v\beta_3$ can be produced in HeLa cells that express $\alpha_v\beta_3$ or 293 cells transfected with the gene for $\alpha_v\beta_3$.

The chimeric penton base protein may be present in the viral particle with the fiber, without the fiber (in which case the rcPB protein functions as the virus attachment and internalization protein), with a recombinant fiber molecule that is specific for a receptor, such as a cell-specific or tissue-specific receptor, or with a recombinant coat protein that is specific for a receptor, such as a cell-specific or tissue-specific receptor. See Examples 4–9 for a further description of these embodiments of the invention.

Recombinant adenoviruses of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly, or DNA encoding ribozymes or antisense molecules, for example. Accordingly, use of the term "therapeutic gene" is intended to encompass these and other embodiments of that which is more commonly referred to as gene therapy and is known to those of skill in the art. Diseases that are candidates for such treatment include, for example, cancer, e.g., melanoma or glioma, cystic fibrosis, genetic disorders, and pathogenic infections, including HIV infection. For example, a recombinant adenovirus having a penton base molecule recognized by $\alpha_v\beta_3$ receptors can be used to treat melanoma or glioma, and a recombinant adenovirus recognized by $\alpha_3\beta_1$ receptors and expressing the cystic fibrosis transmembrane regulator (CFTR) gene can be used to treat cystic fibrosis by delivery to the epithelial cells of the lungs. Furthermore, various blood-related diseases can be treated by using a recombinant adenovirus recognized by $\alpha_m\beta_2$ receptors to target neutrophils and macrophages, a recombinant adenovirus recognized by $\alpha_4\beta_1$ receptors to target lymphocytes, a recombinant adenovirus recognized by $\alpha_{IIb}\beta_3$ receptors to target platelets and megakaryocytes, and a recombinant adenovirus recognized by $\alpha_v\beta_3$ integrins to target endothelial cells undergoing angiogenesis.

One skilled in the art will appreciate that suitable methods of administering a recombinant adenovirus of the present invention to an animal for purposes of gene therapy (see, for example, Rosenfeld et al., *Science*, 252, 431–434 (1991); Jaffe et al., *Clin. Res.*, 39 (2), 302A (1991); Rosenfeld et al., *Clin. Res.*, 39 (2), 311A (1991); Berkner, *BioTechniques*, 6, 616–629 (1988)), chemotherapy, and vaccination are available, and, although more than one route can be used to administer such a recombinant adenovirus, a particular route can provide a more immediate and more effective reaction than another route. Pharmaceutically acceptable excipients are also well-known to those who are skilled in the art, and are readily available. The choice of excipient will be determined in part by the particular method used to administer the recombinant adenovirus. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice;. (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The recombinant adenovirus of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the recombinant adenovirus of the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

In addition to the recombinant adenovirus of the present invention, the adenoviral transfer vector also has utility in vitro. It can be used as a research tool in the study of adenoviral attachment and infection of cells and in a method of assaying receptor-ligand interaction. Similarly, the recombinant penton base protein comprising a nonpenton base amino acid sequence in addition to or in place of a wild-type receptor binding sequence, preferably the RGD sequence, can be used in receptor-ligand assays and as adhesion proteins in vitro or in vivo, for example.

The following examples further illustrate the present invention and, of course, should not be construed as in any way limiting its scope.

EXAMPLE 1

This example describes the construction of the adenoviral transfer vector (pAT) for making chimeric penton base molecules.

pAT, a partial restriction map of which is shown in FIG. 1, was created by cloning the unique Bam HI/Pme I fragment (13259-21561) from the Ad5 genome into pNEB 193 R1-, a minor derivative of pNEB 193 (New England Biolabs, Beverly, Mass.), from which the unique Eco RI restriction site was removed (SEQ ID NO:7). The resulting vector was called pNEB 193 R1- [Ad5 (Bam HI/Pme I)].

Two pairs of PCR primers were synthesized and used to amplify a region upstream (left side) and a region downstream (right side) from the RGD sequence. A unique Spe I site was inserted into the antisense primer (A5a(15147)S, SEQ ID NO:16) used to amplify the upstream region between the RGD sequence and a Bst XI site (15017). The Bst XI site is 35 bp upstream from the penton base start codon (15052). A unique Spe I site was also inserted into the sense primer (A5a(15204)S, SEQ ID NO:15) to amplify the right side of the gene between the RGD amino acid sequence and an Asc I site (15671). The antisense primer (A5a(15659)) used to amplify the right side of the gene is shown as SEQ ID NO:14. The sense primer (A5s(14153)E; SEQ ID NO:13) for the left side of the gene includes the naturally occurring Bst XI site (15017) and also contains a unique Eco RI site 13 bp upstream from the penton base start codon, which is not in the original sequence. Using these primers, the left and right sides of the penton base gene were amplified and then cloned into pNEB 193 R1' [Ad5 (Bam HI/Pme I)] to create the pAT vector.

The net results of this cloning were the generation of a unique Eco RI site just upstream of the penton base start codon (SEQ ID NO:5) to facilitate subcloning into a baculovirus transfer vector and to facilitate the generation of a recombinant adenovirus using the pAT vector; the deletion of an 8 amino acid region (SEQ ID NO:11) within the wild-type penton base containing the $\alpha_v$ integrin binding domain; and the incorporation of a unique Spe I site encoding the amino acids threonine and serine in place of the deleted region (SEQ ID NO:9) so that alternative DNA sequences encoding receptor-binding amino acid motifs or other sequences of amino acids can be inserted at that site.

EXAMPLE 2

Figure 2:
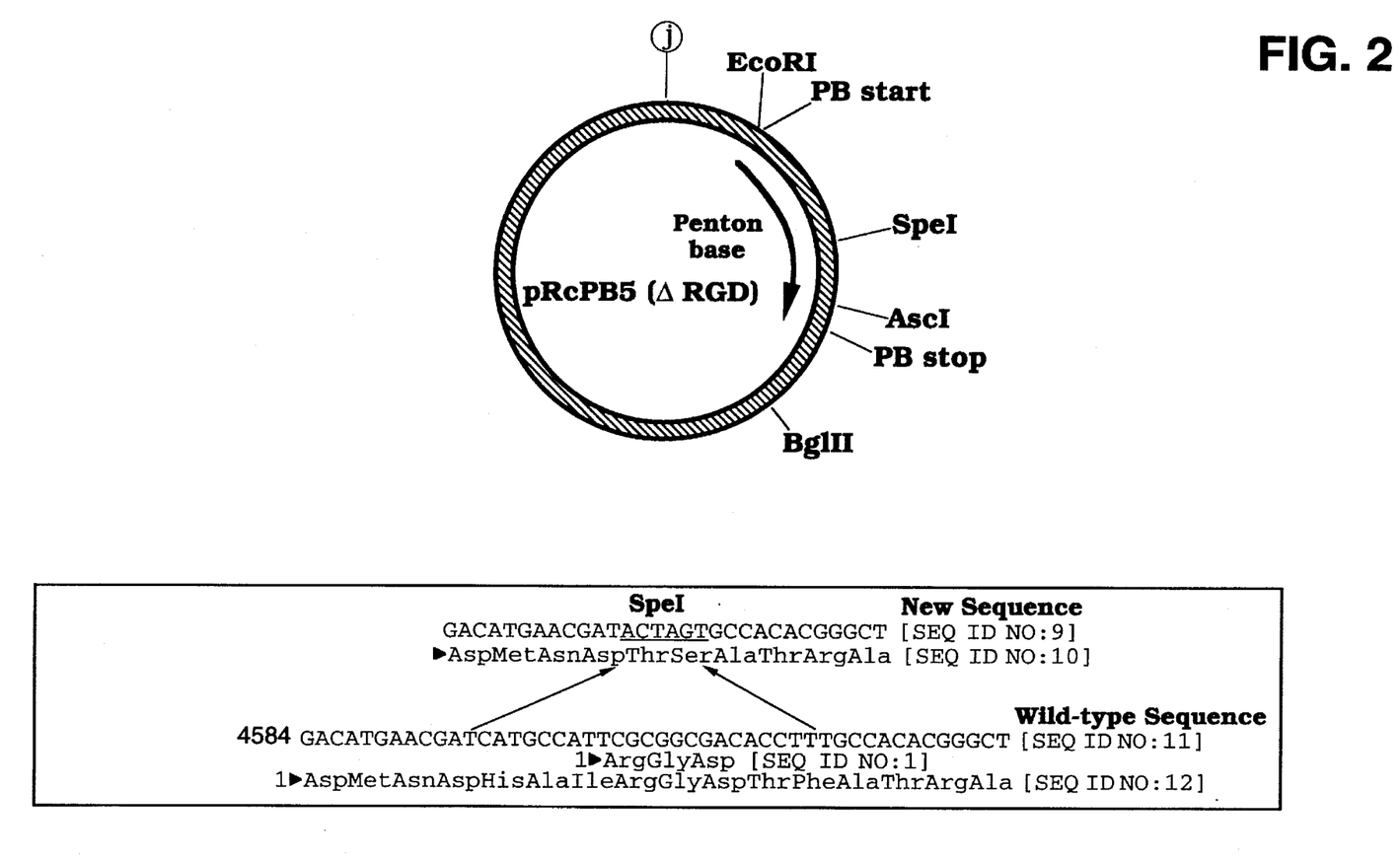
FIG. 2 is a partial restriction map of the vector pRcPB5 (ΔRGD).

This example describes the construction of the base vector pRcPB5 (ΔRGD) for all cloning used to make a recombinant baculovirus for the expression of a recombinant chimeric Ad5 penton base protein (rcPB5 protein) and for making rcPB5 genes for incorporation into pAT and other related vectors.

pRcPB5 (ΔRGD), a partial restriction map of which is shown in FIG. 2, was created by cloning the Eco RI/Bgl II fragment from pAT into the baculovirus transfer vector pAcSG2 (Pharmingen, San Diego, Calif.). A new sequence encoding a receptor binding domain is inserted into the unique Spe I site within the penton base gene in pRcPB5 (ΔRGD). The resulting vector is then used to generate recombinant baculovirus constructs so that rcPB5 protein can be generated in large quantities and evaluated. Based on evaluation of the recombinant protein, the Eco RI/Bgl II fragment from the pRcPB5 derivative is then cloned into pAT to make the recombinant adenovirus (Ad5 rcPB).

EXAMPLE 3

This example describes the cloning of integrin sequences into the Spe I site of the pRcPB5 (ΔRGD) vector of Example 2.

A sequence recognized by a specific integrin receptor is cloned into the penton base cassette as follows. Overlapping sense and antisense oligonucleotides encoding a desired integrin-specific sequence are synthesized. For example, the overlapping sense (Beta 3RGDs, SEQ ID NO:19) and antisense (Beta 3RGDa, SEQ ID NO:20) oligonucleotides that encode sequences that are specific for the integrin $\alpha_v\beta_3$ (SEQ ID NO:17) and the overlapping sense (CS-1s, SEQ ID NO:23) and antisense (CS-1a, SEQ ID NO:24) oligonucleotides that encode sequences that are specific for the integrin $\alpha_4\beta_1$ are synthesized. The sense and antisense sequences for each are mixed and converted to full-length double-stranded sequences by filling in the unpaired nucleotides with Klenow fragment. The resulting double-stranded sequence is then inserted into the Spe I site of the pRcPB5 (ΔRGD) vector following digestion with the endonucleases Xba I and Spe I. The resulting vectors, pRcPB5($\alpha_v\beta_3$) and pRCPB5($\alpha_4\beta_1$), are used to create the recombinant baculovirus vectors, AcNPV rcPB5($\alpha_v\beta_3$) and AcNPV rcPB5($\alpha_4\beta_1$). The rcPB5 protein produced in insect cells using the aforementioned baculovirus vectors is evaluated as described above. Based on the analyses in the baculovirus expression system, the Eco RI/Bgl II fragment from each of the vectors then is cloned into a pAT vector to produce the adenoviral vectors, pAT rcPB5 ($\alpha_v\beta_3$) and pAT rcPB5($\alpha_4\beta_1$).

EXAMPLE 4

This example illustrates the creation of recombinant adenovirus particles containing a wild-type fiber protein and a chimeric penton base specific for $\alpha_4$ integrins (Ad5 rcPB5 ($\alpha_4$):wtFiber).

A chimeric penton base specific for $\alpha_4$ integrin (Ad5 rcPB5 ($\alpha_4$):wtFiber) can be constructed through ligation of plasmid DNA with viral DNA, which chimeric construct then can be transfected into cells using standard methods. The pAT vector containing the desired chimeric form of penton base is digested with Xmn I to generate a 1 kb piece of DNA containing the receptor-specific coding sequence. Ad5 DNA is digested with the restriction endonuclease Xmn I, which cuts wild-type Ad5 at positions 14561 and 15710 within the Ad5 genome. The two larger fragments are purified away from the smaller 1 kb piece containing the sequence encoding RGD and then ligated with the Xmn I fragment from the pAT vector. The ligated fragments are then transfected into the appropriate cell line to produce recombinant virus. The virus produced from the cells can be plaque purified and verified to contain the chimeric penton base gene using PCR. The penton base produced in the Ad5-infected cells can be also purified, and its receptor-specificity verified.

EXAMPLE 5

This example illustrates the creation of recombinant adenovirus particles containing wild-type fiber protein and chimeric penton base specific for $\alpha_4$ integrins (Ad5 rcPB5 ($\alpha_4$):wtFiber).

Adenovirus particles having a chimeric penton base specific for $\alpha_4$ integrins (Ad5 rcPB5 ($\alpha_4$):wtFiber) can be constructed through transfection of plasmid DNA and viral DNA into cells and generation of recombinants through homologous recombination. The pAT vector containing the desired chimeric form of penton base is linearized by digestion with Bam HI. Ad5 DNA is digested with the restriction endonuclease Xmn I which cuts wild type Ad5 at positions 14561 and 15710 within the Ad5 genome. These two unique sites within the Ad5 genome flank the Spe I site in the pAT vector. The linearized pAT vector and the Xmn I-digested Ad5 DNA are then transfected into the appropriate cell line, such as 293 cells, to produce a recombinant virus by homologous recombination. The virus produced from such cells can be plaque purified and verified to contain the chimeric penton base gene using PCR. The penton base produced in Ad5-infected cells also can be purified, and its receptor-specificity verified.

EXAMPLE 6

This example illustrates the creation of recombinant adenovirus particles lacking fiber protein and chimeric penton base specific for $\alpha_4$ integrins (Ad5 rcPB5 ($\alpha_4$):-Fiber).

The Ad5 rcPB5 ($\alpha_4$):wtFiber viral DNA can be digested with Bam HI and the 0-59 map unit (m.u.) fragment purified. The fiber gene can be deleted from plasmid containing the Ad5 Bam HI/Sal I fragment (genome map units 59-100). The resultant plasmid is then digested with Bam HI and Sal I, ligated to the 0-59 m.u. piece of Ad5 rcPB5 ($\alpha_4$):wtFiber DNA, and transfected into cells expressing $\alpha_4$ integrins. The $\alpha_4$ integrins can serve as both the attachment and internalization receptors for the Ad5 rcPB5 ($\alpha_4$):-Fiber virus.

EXAMPLE 7

This example illustrates the creation of recombinant adenovirus particles lacking fiber protein and containing chimeric penton base with an epitope recognized by a monoclonal antibody (antibody-specific sequence).

Viral DNA is isolated from an Ad5 virus lacking fiber, as in Example 6, and digested with the endonuclease Xmn I as in Example 5. The pAT vector containing the chimeric penton base gene containing the sequence encoding the antibody-specific epitope is prepared as in Example 5. The digested viral and pAT DNA is transfected into 293 cells to produce virus by homologous recombination. The recombinant virus is passaged and amplified by incubating cell lysates with a bispecific antibody to av integrins (expressed and internalized in 293 cells) and the antibody-specific epitope on the chimeric penton base, thereby allowing the recombinant virus to attach and infect the 293 cells. The virus progeny from infected cells lack the bispecific antibody so that following their purification from infected cells they can be targeted to HIV-infected cells by combining them with a bispecific antibody recognizing the antibody-specific epitope in the chimeric penton base and the HIV gp120.

EXAMPLE 8

This example illustrates the creation of recombinant adenovirus particles containing chimeric fiber protein specific for sialyl Lewis X antigen and chimeric penton base specific for $\alpha_4$ integrins [Ad5 rcPB5 ($\alpha_4$):rcFiber (sLX)].

The protein P-selectin binds to sialyl Lewis X antigen present on lymphocytes. The binding domain from P-selectin is present on the rcFiber (sLX) protein to mediate virus binding. The left arm (0-59 m.u.) of the Ad5 rcPB5 ($\alpha_4$):wtFiber virus can be prepared by Bam HI digestion and then purified.

The rcFiber (sLX) gene can be cloned into the plasmid containing the 59-100 m.u. fragment of the Ad5 genome. The rcFiber (sLX) gene then can replace the wtFiber gene. The 59-100 m.u. Ad5 fragment containing rcFiber (sLX) then can be ligated to the 0-59 m.u. Ad5 fragment containing rcPB5 ($\alpha_4$). The ligated fragment then can be transfected into cells expressing the receptors for attachment (sialyl Lewis X) and internalization ($\alpha_4$ integrins) for the chimeric virus Ad5 rcPB5 ($\alpha_4$):rcFiber (sLX).

EXAMPLE 9

This example illustrates the creation of recombinant adenovirus particles containing chimeric hexon protein specific for sialyl Lewis X antigen, chimeric penton base specific for $\alpha_4$ integrins, and lacking fiber protein [Ad5 rcPB5 ($\alpha_4$):-Fiber:rcHexon (sLX)].

The protein P-selectin binds to sialyl Lewis X antigen present on lymphocytes. The binding domain from P-selection is present within an exposed loop on wtHexon, and the resultant rcHexon (sLX) protein can mediate virus binding. Genes encoding rcPB5 ($\alpha_4$) and rcHexon (sLX) can be cloned into the pAT vector that contains the penton base gene and the region encoding the exposed loop of hexon protein. A ligation of three fragments can be performed to generate the recombinant virus. Ad5 rcPB5 ($\alpha_4$):-Fiber virus may be digested with Eco RI and Bam HI. The left end of the genome up to the Eco RI site and the right end of the genome down to the Bam HI site can be purified and ligated with the Eco RI/Bam HI fragment from the pAT vector containing rcPB5 ($\alpha_4$) and rcHexon (sLX). The ligated fragment then can be transfected into cells expressing the receptors for attachment (sialyl Lewis X) and internalization ($\alpha_4$ integrins) for the chimeric virus Ad5 rcPB5 ($\alpha_4$):rcFiber (sLX).

EXAMPLE 10

This example describes the expression of wild-type Ad5 and mutant rcPB5 ($\Delta$RGD) penton base protein in baculovirus.

Using PCR, the wild-type Ad5 penton base sequence was amplified with an Eco RI site inserted at the 5' end of the gene. This gene was then cloned into the pAT vector and then subcloned into the pAcSG2 baculoviral transfer vector, using methods known in the art. Recombinant baculovirus encoding the Ad5 penton base gene (AcNPV wtPB5) produced levels of penton base protein in insect cells that constituted approximately 50% of the total cellular protein. The purified wtPB5 protein migrated consistently with respect to its known molecular weight on SDS-PAGE and can mediate cell adhesion like Ad2 penton base (Wickham et al. (1993), supra).

The core baculoviral transfer vector, pRcPB5 ($\Delta$RDG), for expression of rcPB5 protein in the baculoviral expression system, has been used to make recombinant baculovirus, which expresses rcPB5 protein. This rcPB5 protein, rcPB5 ($\Delta$RGD), contains an 8 amino acid deletion in the RGD region as shown in FIG. 2, which is a partial restriction map of the vector pRcPB5 (ΔRGD). This protein migrates consistently with respect to its known molecular weight on SDS-PAGE and, in contrast to the wild-type protein (wtPB5), does not mediate cell adhesion, which is consistent with its lack of the RGD cell adhesion motif. Chimeric recombinant penton base molecules rcPB5 ($\alpha_v\beta_3$) and rcPB5 ($\alpha_4$), each containing inserts specific for $\alpha_v\beta_3$ and $\alpha_4$ integrins, respectively, also have been produced via the core baculoviral transfer vector, pRcPB5 (ΔRGD). The rcPB5 ($\alpha_v\beta_3$) protein mediates epithelial cell ($\alpha_v$+, $\alpha_4$−), but not lymphocyte ($\alpha_v$−, $\alpha_4$+), adhesion; in contrast, RcPB5 ($\alpha_4$) supports lymphocyte, but not epithelial cell, adhesion.

EXAMPLE 11

This example illustrates the targeting of adenovirus to lymphocytes.

The transfer vectors pAT ($\alpha_v\beta_3$) and pAT ($\alpha_4$) were created by cloning the Eco RI/Bgl II fragments from their respective pRcPB5 vectors into the pAT (ΔRGD) vector. These pAT vectors were then linearized by Bam HI digestion and transfected with Xmn I-digested viral DNA from an Ad5 variant, which lacks the E1 and E3 regions and contains a β-galactosidase reporter gene under control of a CMV promoter; to obtain recombinant Ad5 virus, namely Ad5 rcPB (ΔRGD), Ad5 rcPB ($\alpha_v\beta_3$), and Ad5 rcPB ($\alpha_4$), through homologous recombination. The Xmn I endonuclease cuts the wild-type Ad5 at positions 14561 and 15710 within the genome, while the Bam HI/Pme I fragment contained in the pAT vector spans the Ad5 region of 13258 to 21562. Thus, the regions of homologous overlap between the left and right viral sequences with the Bam HI/Pme I fragment are 1303 bp and 5851 bp, respectively. The presence of the chimeric inserts in the Ad5 rcPB ($\alpha_v\beta_3$) and Ad5 rcPB ($\alpha_4$) viruses are verified through PCR.

The recombinant adenovirus Ad5 rcPB ($\alpha_4$) is analyzed for its targeting potential in relation to wild-type Ad5 and recombinant Ad5 rcPB (ΔRGD) by measuring levels of the reporter gene expression in cells exposed to each of the viruses. Delivery of β-galactosidase to the B-lymphocyte cell line, Ramos, is significantly higher using the Ad5 rcPB ($\alpha_4$) virus than the Ad5 rcPB (ΔRGD) and wild-type Ad5 viruses. Conversely, delivery of β-galactosidase to an epithelial-derived cell line is significantly higher than the wild-type Ad5 virus in comparison to the Ad5 rcPB ($\alpha_4$) and Ad5 rcPB (ΔRGD) viruses. These results demonstrate that changes in penton base protein that redirect the protein to interact with a new receptor can be utilized to target the virus to new cells and tissues while specifically avoiding delivery to other cells and tissues.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A recombinant adenovirus comprising (a) a chimeric penton base protein, wherein said chimeric penton base protein comprises a nonpenton base amino acid sequence, which is (i) specific for binding to a receptor, (ii) an antibody domain or (iii) an epitope, in addition to or in place of a wild-type penton base amino acid sequence, which is specific for binding to a receptor, and (b) a therapeutic gene that is capable of being expressed in a cell to which the recombinant adenovirus has attached or by which the recombinant adenovirus has been internalized.

2. The recombinant adenovirus of claim 1, wherein said wild-type penton base amino acid sequence is an RGD amino acid sequence.

3. The recombinant adenovirus of claim 2, wherein said recombinant adenovirus is fiberless.

4. The recombinant adenovirus of claim 2, which further comprises, in addition to the chimeric penton base protein, a chimeric coat protein which includes an amino acid sequence that is (i) specific for binding to a receptor, (ii) an antibody domain or (iii) an epitope.

5. The recombinant adenovirus of claim 4, wherein said amino acid sequence in said chimeric coat protein, which is (i) specific for binding to a receptor, (ii) an antibody domain or (iii) an epitope, (i) is specific for binding to the same receptor, (ii) is the same antibody domain or (iii) is the same epitope as the nonpenton base amino acid sequence in said chimeric penton base protein.

6. The recombinant adenovirus of claim 4, wherein said chimeric coat protein is selected from the group consisting of a chimeric fiber and a chimeric hexon.

7. The recombinant adenovirus of claim 6, wherein said amino acid sequence in said chimeric coat protein, which is (i) specific for binding to a receptor, (ii) an antibody domain or (iii) an epitope, (i) is specific for binding to the same receptor, (ii) is the same antibody domain or (iii) is the same epitope as the nonpenton base amino acid sequence in said chimeric penton base protein.

8. A recombinant baculovirus comprising a chimeric adenoviral penton base gene sequence encoding a chimeric penton base protein, which chimeric adenoviral penton base gene sequence comprises (a) a nonpenton base gene sequence encoding an amino acid sequence that is (i) specific for binding to a receptor, (ii) an antibody domain or (iii) an epitope, and (b) a wild-type penton base gene sequence that encodes an amino acid sequence that is specific for binding to a receptor.

9. The recombinant baculovirus of claim 8, wherein said wild-type penton base gene sequence encodes an RGD amino acid sequence.

10. The recombinant baculovirus of claim 9, wherein the gene sequence encoding the RGD amino acid sequence has been mutated.

11. The recombinant baculovirus of claim 10, wherein the gene sequence encoding the RGD amino acid sequence has been mutated by insertion of the nonpenton base gene sequence into the gene sequence encoding the RGD amino acid sequence.

12. The recombinant baculovirus of claim 9, wherein the gene sequence encoding the RGD amino acid sequence has been moved within the penton base gene sequence such that in the chimeric penton base protein the RGD amino acid sequence is conformationally inaccessible for binding to a receptor.

13. The recombinant baculovirus of claim 12, wherein the gene sequence encoding the RGD amino acid sequence has been moved within the penton base gene sequence by insertion of the nonpenton base gene sequence near the gene sequence encoding the RGD amino acid.

14. A recombinant baculovirus comprising a chimeric adenoviral penton base gene sequence, wherein said chimeric adenoviral penton base gene sequence includes a nonpenton base gene sequence, which encodes an amino acid sequence that is (i) specific for binding to a receptor, (ii) an antibody domain or (iii) an epitope, in place of a wild-type penton base gene sequence that encodes an amino acid sequence that is specific for binding to a receptor.

15. The recombinant baculovirus of claim 14, wherein said wild-type penton base gene sequence encodes an RGD amino acid sequence.

16. A chimeric adenoviral penton base protein comprising a nonpenton base amino acid sequence, which is (i) specific for binding to a receptor, (ii) an antibody domain or (iii) epitope, in addition to or in place of a wild-type penton base amino acid sequence, which is specific for binding to a receptor.

17. The chimeric adenoviral penton base protein of claim 16, wherein said wild-type penton base amino acid sequence is an RGD amino acid sequence.

18. A viral transfer vector comprising a chimeric adenoviral penton base gene sequence encoding a chimeric penton base protein, which chimeric adenoviral penton base gene sequence comprises a nonpenton base gene sequence encoding an amino acid sequence that is (i) specific for binding to a receptor, (ii) an antibody domain or (iii) an epitope, in addition to a wild-type penton base gene sequence that encodes an amino acid sequence that is specific for binding to a receptor.

19. The viral transfer vector of claim 18, wherein said viral transfer vector is an adenoviral transfer vector.

20. The viral transfer vector of claim 19, wherein said wild-type penton base gene sequence encodes an RGD amino acid sequence.

21. The viral transfer vector of claim 20, wherein the gene sequence encoding the RGD amino acid sequence has been mutated.

22. The viral transfer vector of claim 21, wherein the gene sequence encoding the RGD amino acid sequence has been mutated by insertion of the nonpenton base gene sequence into the gene sequence encoding the RGD amino acid sequence.

23. The viral transfer vector of claim 20, wherein the gene sequence encoding the RGD amino acid sequence has been moved within the penton base gene sequence such that in the chimeric penton base protein the RGD amino acid sequence is conformationally inaccessible for binding to a receptor.

24. The viral transfer vector of claim 23, wherein the gene sequence encoding the RGD amino acid sequence has been moved by insertion of the nonpenton base gene sequence near the gene sequence encoding the RGD amino acid sequence.

25. A viral transfer vector comprising a chimeric adenoviral penton base gene sequence encoding a chimeric penton base protein, which chimeric adenoviral penton base gene sequence comprises a nonpenton base gene sequence encoding an amino acid sequence that is (i) specific for binding to a receptor, (ii) an antibody domain or (iii) an epitope, in place of a wild-type penton base gene sequence that encodes an amino acid sequence that is specific for binding to a receptor.

26. The viral transfer vector of claim 25, wherein said viral transfer vector is an adenoviral transfer vector.

27. The viral transfer vector of claim 26, wherein said wild-type penton base gene sequence encodes an RGD amino acid sequence.

28. A prokaryotic or eukaryotic expression vector comprising a chimeric adenoviral penton base gene sequence encoding a chimeric penton base protein, which chimeric adenoviral penton base gene sequence comprises a nonpenton base gene sequence encoding an amino acid sequence that is (i) specific for binding to a receptor, (ii) an antibody domain or (iii) an epitope, in place of a wild-type penton base gene sequence that encodes an amino acid sequence that is specific for binding to a receptor.

29. The prokaryotic or eukaryotic expression vector of claim 28, wherein said wild-type penton base gene sequence encodes an RGD amino acid sequence.

30. A prokaryotic or eukaryotic expression vector comprising a chimeric adenoviral penton base gene sequence encoding a chimeric penton base protein, which chimeric adenoviral penton base gene sequence comprises a nonpenton base gene sequence encoding an amino acid sequence that is (i) specific for binding to a receptor, (ii) an antibody domain or (iii) an epitope, in addition to a wild-type penton base gene sequence that encodes an amino acid sequence that is specific for binding to a receptor.

31. The prokaryotic or eukaryotic expression vector of claim 30, wherein said wild-type penton base gene sequence encodes an RGD amino acid sequence.

32. The prokaryotic or eukaryotic expression vector of claim 31, wherein the gene sequence encoding the RGD amino acid sequence has been mutated.

33. The prokaryotic or eukaryotic expression vector of claim 32, wherein the gene sequence encoding the RGD amino acid sequence has been mutated by insertion of the nonpenton base gene sequence into the gene sequence encoding the RGD amino acid sequence.

34. The prokaryotic or eukaryotic expression vector of claim 31, wherein the gene sequence encoding the RGD amino acid sequence has been moved within the penton base gene sequence such that in the chimeric penton base protein the RGD amino acid sequence is conformationally inaccessible for binding to a receptor.

35. The prokaryotic or eukaryotic expression vector of claim 34, wherein the gene sequence encoding the RGD amino acid sequence has been moved by insertion of the nonpenton base gene sequence near the gene sequence encoding the RGD amino acid sequence.

* * * * *

UNITED STATES PATENT AND TRADEMARK OFFICE
CERTIFICATE OF CORRECTION

PATENT NO. : 5,559,099
DATED : September 24, 1996
INVENTOR(S) : Wickham, et. al.

It is certified that error appears in the above-indentified patent and that said Letters Patent is hereby corrected as shown below:

ON THE TITLE PAGE: item
[75] Inventors: "Joseph T. Brader" should read --Joseph T. Bruder--.

In Column 2, line 12: "$\alpha_{IIb}62_3$" should read --$\alpha_{IIb}\beta_3$--.

In Column 7, line 13: "$\alpha_2$-containing" should read --$\beta_2$-containing--.

Signed and Sealed this

Twenty-eighth Day of January, 1997

Attest:

BRUCE LEHMAN

Attesting Officer   Commissioner of Patents and Trademarks

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Arg Gly Asp
1

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

Lys Gln Ala Gly Asp
1               5

( 2 ) INFORMATION FOR SEQ ID NO:3:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:3:

Glu Ile Leu Asp Val
1               5

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

Asn Pro Xaa Tyr
1

(2) INFORMATION FOR SEQ ID NO:5:

(i) SEQUENCE CHARACTERISTICS:
    (A) LENGTH: 65 base pairs
    (B) TYPE: nucleic acid
    (C) STRANDEDNESS: double
    (D) TOPOLOGY: unknown (ii) MOLECULE TYPE: DNA (genomic)

(ix) FEATURE:
    (A) NAME/KEY: CDS
    (B) LOCATION: 51..65

(xi) SEQUENCE DESCRIPTION: SEQ ID NO:5:

CTCACCAAGG CCATGGCACC GAGCGTTGGT TTTCTTGAAT TCCCCTTAGT ATG CGG        56
                                                           Met Arg
                                                             1

CGC GCG GCG                                                           65
Arg Ala Ala
        5

(2) INFORMATION FOR SEQ ID NO:6:

(i) SEQUENCE CHARACTERISTICS:
    (A) LENGTH: 5 amino acids
    (B) TYPE: amino acid
    (D) TOPOLOGY: linear (ii) MOLECULE TYPE: protein (xi) SEQUENCE DESCRIPTION: SEQ ID NO:6:

Met Arg Arg Ala Ala
1               5

(2) INFORMATION FOR SEQ ID NO:7:

(i) SEQUENCE CHARACTERISTICS:
    (A) LENGTH: 65 base pairs
    (B) TYPE: nucleic acid
    (C) STRANDEDNESS: double
    (D) TOPOLOGY: unknown (ii) MOLECULE TYPE: DNA (genomic)

( i x ) FEATURE:
       ( A ) NAME/KEY: CDS
       ( B ) LOCATION: 51..65

( x i ) SEQUENCE DESCRIPTION: SEQ ID NO:7:

CTCACCAAGG CCATGGCACC GAGCGTTGGT TTTCTTGTAT TCCCCTTAGT ATG CGG    56
                                                         Met Arg
                                                          1

CGC GCG GCG                                                       65
Arg Ala Ala
        5

( 2 ) INFORMATION FOR SEQ ID NO:8:

( i ) SEQUENCE CHARACTERISTICS:
              ( A ) LENGTH: 5 amino acids
              ( B ) TYPE: amino acid
              ( D ) TOPOLOGY: linear ( i i ) MOLECULE TYPE: protein ( x i ) SEQUENCE DESCRIPTION: SEQ ID NO:8:

Met Arg Arg Ala Ala
 1               5

( 2 ) INFORMATION FOR SEQ ID NO:9:

( i ) SEQUENCE CHARACTERISTICS:
              ( A ) LENGTH: 30 base pairs
              ( B ) TYPE: nucleic acid
              ( C ) STRANDEDNESS: double
              ( D ) TOPOLOGY: unknown ( i i ) MOLECULE TYPE: DNA (genomic)

( i x ) FEATURE:
              ( A ) NAME/KEY: CDS
              ( B ) LOCATION: 1..30

( x i ) SEQUENCE DESCRIPTION: SEQ ID NO:9:

GAC ATG AAC GAT ACT AGT GCC ACA CGG GCT                           30
Asp Met Asn Asp Thr Ser Ala Thr Arg Ala
 1               5                   10

( 2 ) INFORMATION FOR SEQ ID NO:10:

( i ) SEQUENCE CHARACTERISTICS:
              ( A ) LENGTH: 10 amino acids
              ( B ) TYPE: amino acid
              ( D ) TOPOLOGY: linear ( i i ) MOLECULE TYPE: protein ( x i ) SEQUENCE DESCRIPTION: SEQ ID NO:10:

Asp Met Asn Asp Thr Ser Ala Thr Arg Ala
 1               5                   10

( 2 ) INFORMATION FOR SEQ ID NO:11:

( i ) SEQUENCE CHARACTERISTICS:
              ( A ) LENGTH: 48 base pairs
              ( B ) TYPE: nucleic acid
              ( C ) STRANDEDNESS: double
              ( D ) TOPOLOGY: unknown ( i i ) MOLECULE TYPE: DNA (genomic)

( i x ) FEATURE:
              ( A ) NAME/KEY: CDS
              ( B ) LOCATION: 1..48

(xi) SEQUENCE DESCRIPTION: SEQ ID NO:11:

| GAC | ATG | AAC | GAT | CAT | GCC | ATT | CGC | GGC | GAC | ACC | TTT | GCC | ACA | CGG | GCT | 48 |
| Asp | Met | Asn | Asp | His | Ala | Ile | Arg | Gly | Asp | Thr | Phe | Ala | Thr | Arg | Ala | |
| 1 | | | | 5 | | | | | 10 | | | | | 15 | | |

(2) INFORMATION FOR SEQ ID NO:12:

(i) SEQUENCE CHARACTERISTICS:
        (A) LENGTH: 16 amino acids
        (B) TYPE: amino acid
        (D) TOPOLOGY: linear     (ii) MOLECULE TYPE: protein     (xi) SEQUENCE DESCRIPTION: SEQ ID NO:12:

| Asp | Met | Asn | Asp | His | Ala | Ile | Arg | Gly | Asp | Thr | Phe | Ala | Thr | Arg | Ala |
| 1 | | | | 5 | | | | | 10 | | | | | 15 | |

(2) INFORMATION FOR SEQ ID NO:13:

(i) SEQUENCE CHARACTERISTICS:
        (A) LENGTH: 52 bases
        (B) TYPE: nucleic acid
        (C) STRANDEDNESS: single
        (D) TOPOLOGY: unknown     (ii) MOLECULE TYPE: DNA (synthetic)

(xi) SEQUENCE DESCRIPTION: SEQ ID NO:13:

AAAACTCACC AAGGCCATGG CACCGAGCGT TGGTTTTCTT GAATTCCCCT TA    52

(2) INFORMATION FOR SEQ ID NO:14:

(i) SEQUENCE CHARACTERISTICS:
        (A) LENGTH: 25 bases
        (B) TYPE: nucleic acid
        (C) STRANDEDNESS: single
        (D) TOPOLOGY: unknown     (ii) MOLECULE TYPE: DNA (synthetic)

(xi) SEQUENCE DESCRIPTION: SEQ ID NO:14:

CTGGCGGGCG CGCCAAAATC TGGTT    25

(2) INFORMATION FOR SEQ ID NO:15:

(i) SEQUENCE CHARACTERISTICS:
        (A) LENGTH: 26 bases
        (B) TYPE: nucleic acid
        (C) STRANDEDNESS: single
        (D) TOPOLOGY: unknown     (ii) MOLECULE TYPE: DNA (synthetic)

(xi) SEQUENCE DESCRIPTION: SEQ ID NO:15:

AAAACTAGTG CCACACGGGC TGAGGA    26

(2) INFORMATION FOR SEQ ID NO:16:

(i) SEQUENCE CHARACTERISTICS:
        (A) LENGTH: 26 bases
        (B) TYPE: nucleic acid
        (C) STRANDEDNESS: single
        (D) TOPOLOGY: unknown     (ii) MOLECULE TYPE: DNA (synthetic)

(xi) SEQUENCE DESCRIPTION: SEQ ID NO:16:

```
AAAACTAGTA TCGTTCATGT CCTCCA                                                         26
```

( 2 ) INFORMATION FOR SEQ ID NO:17:

( i ) SEQUENCE CHARACTERISTICS:
           ( A ) LENGTH: 68 base pairs
           ( B ) TYPE: nucleic acid
           ( C ) STRANDEDNESS: double
           ( D ) TOPOLOGY: unknown       ( i i ) MOLECULE TYPE: DNA (genomic)

( i x ) FEATURE:
           ( A ) NAME/KEY: CDS
           ( B ) LOCATION: 3..68

( x i ) SEQUENCE DESCRIPTION: SEQ ID NO:17:

```
AA ACT AGT GGA GGA TGC TCT TTT GGC CGC GGC GAC ATT CGC AAC TGC          47
   Thr Ser Gly Gly Cys Ser Phe Gly Arg Gly Asp Ile Arg Asn Cys
    1           5                   10                  15

GGC GGC CTG CAG TCT AGA AAA                                             68
Gly Gly Leu Gln Ser Arg Lys
              20
```

( 2 ) INFORMATION FOR SEQ ID NO:18:

( i ) SEQUENCE CHARACTERISTICS:
           ( A ) LENGTH: 22 amino acids
           ( B ) TYPE: amino acid
           ( D ) TOPOLOGY: linear       ( i i ) MOLECULE TYPE: protein       ( x i ) SEQUENCE DESCRIPTION: SEQ ID NO:18:

```
Thr Ser Gly Gly Cys Ser Phe Gly Arg Gly Asp Ile Arg Asn Cys Gly
 1           5                   10                  15

Gly Leu Gln Ser Arg Lys
              20
```

( 2 ) INFORMATION FOR SEQ ID NO:19:

( i ) SEQUENCE CHARACTERISTICS:
           ( A ) LENGTH: 41 bases
           ( B ) TYPE: nucleic acid
           ( C ) STRANDEDNESS: single
           ( D ) TOPOLOGY: unknown       ( i i ) MOLECULE TYPE: DNA (synthetic)

( x i ) SEQUENCE DESCRIPTION: SEQ ID NO:19:

```
AAACTAGTGG AGGATGCTCT TTTGGCCGCG GCGACATTCG C                           41
```

( 2 ) INFORMATION FOR SEQ ID NO:20:

( i ) SEQUENCE CHARACTERISTICS:
           ( A ) LENGTH: 42 bases
           ( B ) TYPE: nucleic acid
           ( C ) STRANDEDNESS: single
           ( D ) TOPOLOGY: unknown       ( i i ) MOLECULE TYPE: DNA (synthetic)

( x i ) SEQUENCE DESCRIPTION: SEQ ID NO:20:

```
TTTTCTAGAC TGCAGGCCGC CGCAGTTGCG AATGTCGCCG CG                          42
```

( 2 ) INFORMATION FOR SEQ ID NO:21:

( i ) SEQUENCE CHARACTERISTICS:
           ( A ) LENGTH: 110 base pairs (B) TYPE: nucleic acid
(C) STRANDEDNESS: double
(D) TOPOLOGY: unknown (ii) MOLECULE TYPE: DNA (genomic)

(ix) FEATURE:
(A) NAME/KEY: CDS
(B) LOCATION: 3..110

(xi) SEQUENCE DESCRIPTION: SEQ ID NO:21:

```
AA ACT AGT GGA GGA GAC GAG CTC CCA CAG CTC GTG ACT CTC CCA CAC      47
   Thr Ser Gly Gly Asp Glu Leu Pro Gln Leu Val Thr Leu Pro His
   1               5                   10                  15

CCA AAC CTC CAC GGT CCA GAG ATT CTC GAC GTG CCA TCT ACT GGC GGC      95
Pro Asn Leu His Gly Pro Glu Ile Leu Asp Val Pro Ser Thr Gly Gly
                20                  25                  30

CTG CAG TCT AGA AAA                                                 110
Leu Gln Ser Arg Lys
            35
```

(2) INFORMATION FOR SEQ ID NO:22:

(i) SEQUENCE CHARACTERISTICS:
(A) LENGTH: 36 amino acids
(B) TYPE: amino acid
(D) TOPOLOGY: linear (ii) MOLECULE TYPE: protein (xi) SEQUENCE DESCRIPTION: SEQ ID NO:22:

```
Thr Ser Gly Gly Asp Glu Leu Pro Gln Leu Val Thr Leu Pro His Pro
1               5                   10                  15

Asn Leu His Gly Pro Glu Ile Leu Asp Val Pro Ser Thr Gly Gly Leu
                20                  25                  30

Gln Ser Arg Lys
            35
```

(2) INFORMATION FOR SEQ ID NO:23:

(i) SEQUENCE CHARACTERISTICS:
(A) LENGTH: 65 bases
(B) TYPE: nucleic acid
(C) STRANDEDNESS: single
(D) TOPOLOGY: unknown (ii) MOLECULE TYPE: DNA (synthetic)

(xi) SEQUENCE DESCRIPTION: SEQ ID NO:23:

AAACTAGTGG AGGAGACGAG CTCCCACAGC TCGTGACTCT CCCACACCCA AACCTCCACG     60

GTCCA                                                                 65

(2) INFORMATION FOR SEQ ID NO:24:

(i) SEQUENCE CHARACTERISTICS:
(A) LENGTH: 60 bases
(B) TYPE: nucleic acid
(C) STRANDEDNESS: single
(D) TOPOLOGY: unknown (ii) MOLECULE TYPE: DNA (synthetic)

(xi) SEQUENCE DESCRIPTION: SEQ ID NO:24:

TTTTCTAGAC TGCAGGCCGC CAGTAGATCG CACGTCGAGA ATCTCTGGAC CGTGGAGGTT     60